United States Patent
Endo

(10) Patent No.: US 7,031,431 B2
(45) Date of Patent: Apr. 18, 2006

(54) RADIOLOGICAL IMAGING APPARATUS AND METHOD

(75) Inventor: Tadao Endo, Saitama (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 11/112,821

(22) Filed: Apr. 22, 2005

(65) Prior Publication Data

US 2005/0184243 A1    Aug. 25, 2005

Related U.S. Application Data

(63) Continuation of application No. 10/464,039, filed on Jun. 18, 2003, now Pat. No. 6,904,126.

(30) Foreign Application Priority Data

Jun. 19, 2002    (JP) ............................. 2002-178801

(51) Int. Cl.
  *G01N 23/04* (2006.01)
  *H05G 1/00* (2006.01)
(52) U.S. Cl. ........................................ 378/62; 378/210
(58) Field of Classification Search ............... 378/98.8, 378/98.7, 98.11, 98.12, 108, 19, 901; 250/370.09
See application file for complete search history.

(56) References Cited

U.S. PATENT DOCUMENTS

| 5,454,022 | A | 9/1995 | Lee et al. |
| 5,608,775 | A | 3/1997 | Hassler et al. |
| 6,404,851 | B1 * | 6/2002 | Possin et al. ............... 378/98.7 |
| 6,453,008 | B1 | 9/2002 | Sakaguchi et al. |
| 6,497,511 | B1 * | 12/2002 | Schmitt et al. ............. 378/207 |
| 6,839,407 | B1 | 1/2005 | Nascetti et al. |
| 6,868,138 | B1 * | 3/2005 | Clinthorne et al. ........ 378/98.8 |

* cited by examiner

*Primary Examiner*—Edward J. Glick
*Assistant Examiner*—Irakli Kiknadze
(74) *Attorney, Agent, or Firm*—Morgan & Finnegan, LLP

(57) ABSTRACT

A radiological imaging apparatus and method corrects fixed pattern noise (FPN) generated within the apparatus and suppresses increases in random noise attendant upon FPN correction to provide radiological imaging having improved reliability and image quality. The apparatus has a signal processing circuit that digitizes analog output from a read-out circuit, four FPN memories for storing four dark outputs, a light memory for storing a light output after X-ray exposure of a subject, a CPU for controlling the signal processing circuit as well as FPN and light memories, and a shift resister 7 controlled by the CPU. The method involves averaging multiple dark outputs and subtracting the FPN data average so obtained from the light output which includes the X-ray imaged to enhance picture quality. Since the FPN correction uses FPN data that has been averaged over multiple dark outputs, the method also suppresses random noise generated by the FPN correction for enhanced imaging accuracy.

6 Claims, 8 Drawing Sheets

AVERAGING PROCESS (CALCULATED BY CPU)

FPN CORRECTION DATA $$\sum_{M=1}^{4} FPN_M(i, j) \Big/ 4$$

RADIOLOGICAL IMAGING APPARATUS AND METHOD

This application is a continuation of application Ser. No. 10/464,039, filed Jun. 18, 2003, now U.S. Pat. No. 6,904,126 issued on Jun. 7, 2005.

FIELD OF THE INVENTION

The present invention relates to a radiological imaging apparatus and method, and more particularly, to a radiological imaging apparatus and method used in medical X-ray equipment, industrial non-destructive testing devices and the like.

BACKGROUND OF THE INVENTION

With the conventional still-picture X-ray technology currently in use, the so-called film-based technique is the most prevalent. In this technique, the patient is exposed to X-rays and the X-rays that pass through the body are then exposed onto a sheet of film. The film has the function of displaying and recording information, and is widely used throughout the world due to its capacity to be enlarged, its high degree of gradation, its light weight and ease of handling. On the other hand, the technique suffers from several disadvantages, including a complicated process of developing the image, the problem of long-term storage, and the time and effort involved in manual search and retrieval of the physical images.

By contrast, moving-image photographic systems rely mainly on image intensifier (I.I). Since I.I uses the photoelectron multiplier effect inside the device, it generally has good sensitivity and has the additional advantage of exposing the patient to lower levels of radiation. The I.I technique not only provides the physician with a see-through image of the patient but also, due to the conversion of the CCD analog output to digital output (a process referred to here as digitization), makes possible the computerized recording, display and storage of such data. However, because medical diagnosis requires a high degree of gradation, even with I.I, film is often used for still picture imaging.

Recently, with a growing need to digitize X-ray images inside the hospital itself, in place of film, X-ray imaging devices that use an X-ray sensor with solid-state image sensing elements arrayed two-dimensionally to convert the X-ray image into electrical signals have begun to be used. Since the X-ray image can then be replaced with digital information, image information can be sent instantaneously to distant locations, with the advantage of being able to provide state-of-the-art, high-quality diagnostics even to remote areas. Moreover, if no film is used the space previously required for its storage can be turned to other, more productive uses. If in the future it becomes possible to introduce more advanced and sophisticated image processing techniques, it is possible that diagnostics may to some extent be computerized and therefore automated, without the intervention of a radiologist.

Moreover, in recent years, with the use of amorphous thin-film semiconductors in solid-state image sensing elements, X-ray imaging devices capable of taking still pictures have been developed. Using amorphous silicon thin-film semiconductor production technology, photos exceeding 40 cm a side and capable of completely imaging the human torso have been commercialized. Since the production process itself is relatively simple, it is expected that inexpensive detectors based on this technique will become available in the not-so-distant future. In addition, since amorphous silicon can be produced in thin glass sheets having a thickness of i mm or less, the detector itself can be made very thin and compact, for greater ease of handling.

An X-ray imaging device of the sort described above typically has a photoelectric converter circuit, on which a plurality of photoelectric converters for converting radiation into electrical signals are arranged as in a matrix, and a read-out circuit for reading out the electrical signals form the photoelectric converter circuit. FIG. 7, for example, is a timing chart showing the operation of an X-ray imaging device having nine photoelectric converters S1-1 through S3-3 (including switches (TFT) T1-1–T3-3). As for the photoelectric conversion interval (given in the diagram as the X-ray exposure interval): In a state in which the TFT are all OFF, when the light source (X-rays) are turned ON in pulses, the respective photoelectric converters are struck by the light and a signal electric charge comparable to the amount of light is stored in the converter capacitor. If a fluorescent material is used to convert the X-rays into visible light, then either a light-guiding member for guiding the light made visible in proportion to the number of X-rays to the photoelectric converters may be used or the fluorescent material may be disposed near the electrodes of the photoelectric converters.

It should be noted that the signal electrical charge is held in the converter capacitor after the light source is OFF.

Next, as for the read-out interval: The read-out is accomplished at the S1-1–S3-3, one row at a time, starting with row S1-1–S1-3, then with row S2-1–S2-3, and finally with row S3-1–S3-3. First, a gate pulse is applied from SR1 to the switches (TFT) T1-1–T1-3 gate lines in order to read out the first row S1-1–S1-3. Doing so turns T1-1–T1-3 ON and the signal electrical charge that had been stored in S1-1–S1-3 is sent to the signal lines M1–M3 to which read-out capacitors CM1–CM3 have been added, so that the signal electrical charge is sent to the capacitors CM1–CM3 via the TFT. For example, read-out capacitor CM1 added to signal line M1 is the (three-)sum total of the T1-1–T1-3 gate-source interelectrode capacitance (Cgs). Amps A1–A3 amplify the signal electrical charge sent to signal lines M1–M3.

The amplified signal electrical charge sent to capacitors CL1–CL3 both turns OFF and holds SMPL signal OFF. Next, by imparting a pulse from a shift resister 103 to switches Sr1, Sr2 and Sr3 (in that order) the signals held at CL1–CL3 are then output from an amp 104 in the order CL1, CL2 and CL3. Since analog signal outputs B1, B2 and B3 are output from the amp 104, the entire unit, including the shift resister 103 and the switches Sr1–Sr3, is called an analog multiplexer. Ultimately, one row's worth of photoelectric conversion signals (S1-1, S1-2, S1-3) is output in sequence by the analog multiplexer. The read-out of the second row S2-1–S2-3 is carried out in the same way as the read-out of the first row described above.

If the signals at signals lines M1–M3 are sampled and held at CL1–CL3 by the first row's SMPL signal, then the signal lines M1–M3 can be reset to ground electric potential by a CRES signal and thereafter a G2 gate pulse can be applied. In other words, second-row signal electrical charges from the photoelectric converters S2-1–S2-3 can be transmitted by the SR1 while at the same time the first row's signals are being serially converted by the SR2. In so doing, all the signal electrical charges of the first through third rows of photoelectric converters can be output.

The photoelectric converter circuit operation described above is capable of reading X-ray images.

But in reality the image as such also contains fixed pattern noise generated by the photoelectric converter circuit and the read-out circuit.

There are a number of factors that cause fixed pattern noise, including (A) variations in photoelectric converter dark current, (B) variations in switch leak current, (C) variations in photoelectric converter circuit signal wire capacitors CM1–CM3 and (D) variations in read-out circuit amp (for example A1–A3) offset voltage.

Whereas causes (A) and (B) described above show up as dots in the final image, causes (C) and (D) appear as lines; in each case, they degrade the quality of the image. Therefore, conventionally, this type of fixed pattern noise is read out as a dark output image, which is then subtracted from the X-ray image so as to correct the fixed pattern noise (hereinafter FPN).

The dark output image itself acquired in one of two ways: it is either read in when the unit is shipped from the factory or prior to photographing and then stored in memory as dark output data, or it is obtained just before or just after read-in of an X-ray image.

However, there are problems with the conventional methods of acquiring the dark output image (FPN).

In the former case, when the FPN is set either at shipment or prior to photography, there are two problems:

(a) The dark currents of the photoelectric converters have temperature characteristics, which may be different when the FPN is obtained and when the X-ray image is shot. Such differences in temperature characteristics can prevent the FPN from being fully corrected.

(b) Since the TFT leak current changes over time, the leak current may be different when the FPN is obtained and when the X-ray image is shot, and such differences in leak current can prevent the FPN from being fully corrected.

The technique of reading in the FPN just before or just after taking the X-ray image, although it solves the two problems described above, has a problem of its own:

(c) random noise generated by the photoelectric converter circuit (hereinafter referred to simply as random noise) as well as random noise generated by the read-out circuit, which is not fixed pattern noise and therefore cannot be fully corrected, and which, when processed for elimination, only increases by a factor of $\sqrt{2}$ and degrades the quality of the image.

Random noise is caused by shot noise from the photoelectric converter dark electrical charge and by heat noise (that is, Johnson noise) caused by electron thermal disturbances inside the switches. It is one type of noise that is unavoidable. In addition, if the signal lines M1–M3 have any appreciable internal resistance, that resistance, too, will generate Johnson noise or random noise. The operational amplifier that forms part of the read-out circuit also generates random noise.

The amount or volume of random noise can be determined by focusing on a particular pixel and sampling its dark data several times in order to obtain its dark data distribution. In other words, that distribution is a Gaussian distribution, i.e., noise that has a frequency distribution that follows the Gaussian curve, and can be calculated by obtaining the standard deviation σ.

The dark image output from an X-ray imaging apparatus comprising the photoelectric converter circuit in which the photoelectric converter are arranged in a two-dimensional array, contains both FPN as well as random noise. Moreover, both types of noise appear not only in the dark image output but also in the X-ray image as well. Subtracting the dark image output from the X-ray image cancels the FPN but leaves the random noise uncorrected. Also, between the dark image output and the X-ray image, the random noise itself can differ from one pixel to the next. The random noise generated when reading in the dark image output and the random noise generated when reading in the X-ray image are mutually independent phenomena, so an image in which the former is subtracted from the latter (that is, FPN correction) will have a volume of random noise ($\sqrt{2}\cdot\sigma$) that is $\sqrt{2}$ the volume of random noise before correction (standard deviation σ).

SUMMARY OF THE INVENTION

The present invention has been conceived in light of the foregoing considerations.

According to one aspect of the present invention, preferably, a radiological imaging apparatus for forming X-ray images comprises: a radiation detection unit composed of a plurality of photoelectric converters arrayed in a matrix-like formation for the purpose of detecting and converting radiation from an irradiated subject into electrical signals; a drive control unit operatively connected to the radiation detection unit for the purpose of controlling movement of the radiation detection unit; a read-out unit operatively connected to the radiation detection unit for reading the electrical signals output by the radiation detection unit; and a signal processing unit operatively connected to the read-out unit and the drive control unit for processing the electrical signals read out by the read-out unit, the signal processing unit selecting between a first read-out operation, in which the radiation detection unit is operated with irradiation of a subject, and a second read-out operation, in which the radiation detection unit is operated without irradiation of the subject, the signal processing unit further performing the second read-out operation at least twice, averaging the results of the second read-out operation so as to obtain an average signal value thereof, and subtracting the average signal value from a signal value obtained by the first read-out operation so as to obtain a processed image.

According to another aspect of the present invention, preferably, a radiological imaging method comprises the steps of: detecting and converting radiation from and irradiated subject into electrical signals using a photoelectric converter unit; reading the electrical signals output by the photoelectric converter unit using a read-out unit operatively connected to the photoelectric converter unit; processing the electrical signals connected to the electrical signal read-out unit so as to select between a first read-out operation, in which the subject is irradiated with radiation, and a second read-out operation, in which the subject is not irradiated; performing the second read-out operation at least twice and averaging the results of the second read-out operation so as to obtain an average signal value thereof; and subtracting the average signal value from a signal value obtained by the first read-out operation so as to obtain a processed image.

Other features, effects and advantages of the present invention will be apparent from the following description, taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention, in which.

DETAILED DESCRIPTION OF THE PREFERRED EMBODIMENTS

Figure 1:
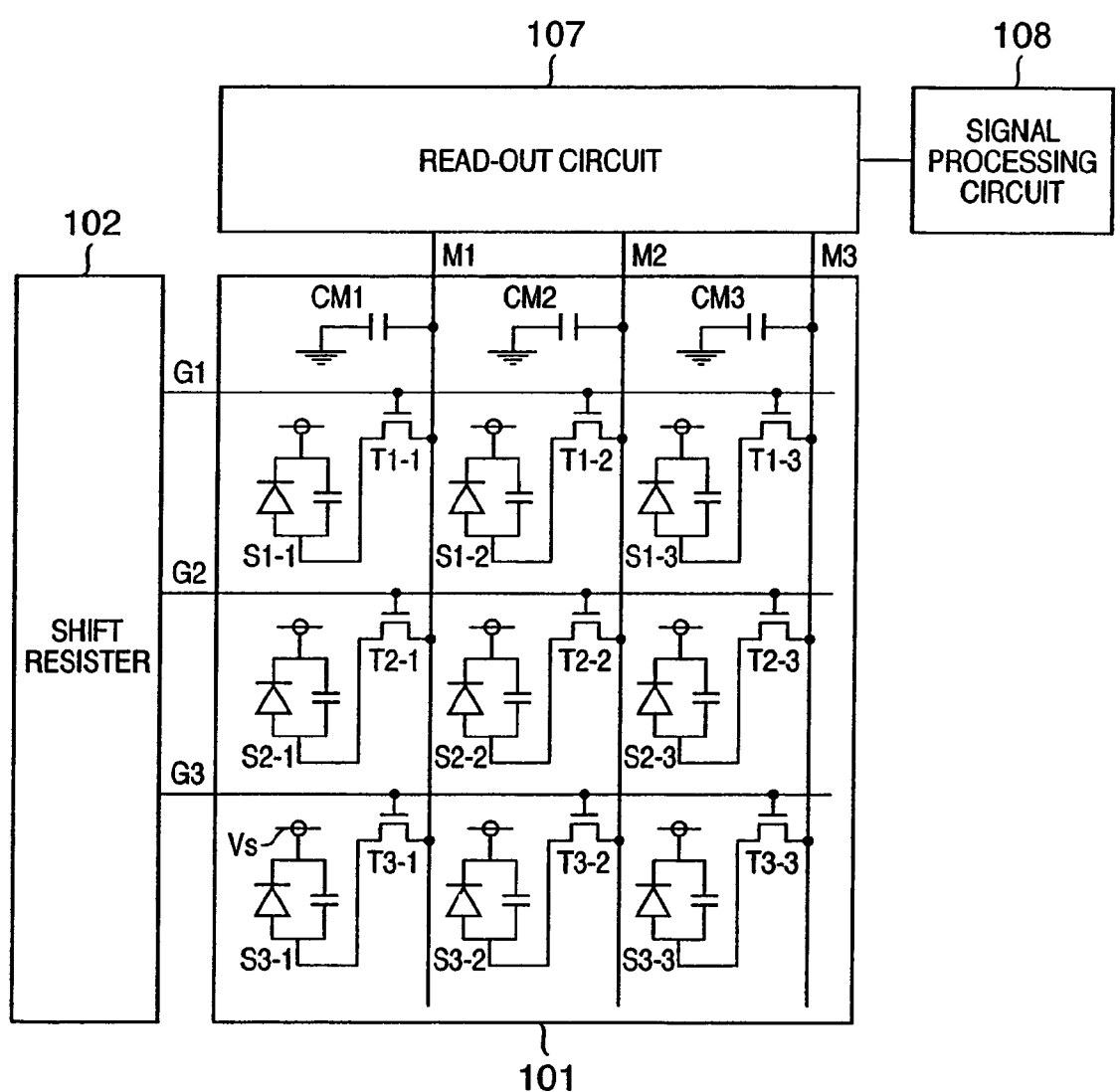
FIG. 1 is a circuit diagram showing schematically the structure of an X-ray imaging apparatus using an amorphous silicon thin film semiconductor according to one embodiment of the present invention.

Preferred embodiments of the present invention are described in detail in accordance with the accompanying drawings, in the first instance FIG. 1.

FIG. 1 is a circuit diagram showing schematically the structure of an imaging apparatus using an amorphous silicon thin film semiconductor according to one embodiment of the present invention, in which the apparatus uses photoelectric converters to take visible light and convert that light into electrical signals.

In this X-ray imaging device, an operator can select between a moving-picture mode and a still-picture mode. It should be noted that FIG. 1 does not show the fluorescent material used to convert the X-rays into visible light, and although the present embodiment is described with reference to X-ray imaging, the present invention is not limited to such but should be understood as being equally applicable to instances involving other types of radiation, such as, for example, alpha-rays, beta-rays or gamma-rays.

In FIG. 1, S1-1–S1-3 denote photoelectric converters arranged in a two-dimensional array. T1-1–T1-3 denotes switches (that is, thin-film transistors, or TFT), G1–G3 denote gate wires that turn the TFT ON/OFF and M1–M3 denote signal lines. Each one of the photoelectric converters is denoted by a photodiode and a capacitor connected in parallel, and is given a reverse bias. That is, the cathode terminal of the photodiode is given a positive (+) bias. The bias lines typically involve joint (common) wiring, which, for convenience, is not shown in FIG. 1. The photoelectrically converted electrical charges are then stored in the capacitors. The entire assemblage of S1-1–S1-3, T1-1–T1-3, G1–G3, signal lines M1-M3 and Vs lines is together called a radiation detection circuit or a photoelectric converter circuit. Reference numeral 102 denotes a shift resister that applies pulses to the gate lines G1–G3 and controls the driving of the photoelectric converters S1-1–S1-3. Reference numeral 107 denotes a read-out circuit that amplifies and serially outputs the parallel signal output of the signal lines M1–M3 inside the photoelectric converter circuit 101.

Reference numeral 108 denotes a signal processing circuit that processes the electrical signals output from the read-out circuit 107.

Each of the photoelectric converters has a wavelength converter for converting the radiation to visible light and a photoelectric converter proper that converts the visible light received into electrical signals. The matrix material of the wavelength converter is a material selected from the group consisting of $Gd_2O_3$, $Gd_2O_2S$ and CsI. The photoelectric converter proper is composed mainly of amorphous silicon. Each of the photoelectric converters is made of a material selected from the group consisting of amorphous silicon, gallium arsenic, mercury iodide and lead iodide. It should be noted that although for convenience of explanation the foregoing description uses the example of a 3×3-pixel photoelectric converter, in reality many more photoelectric converters are arrayed.

Figure 2:
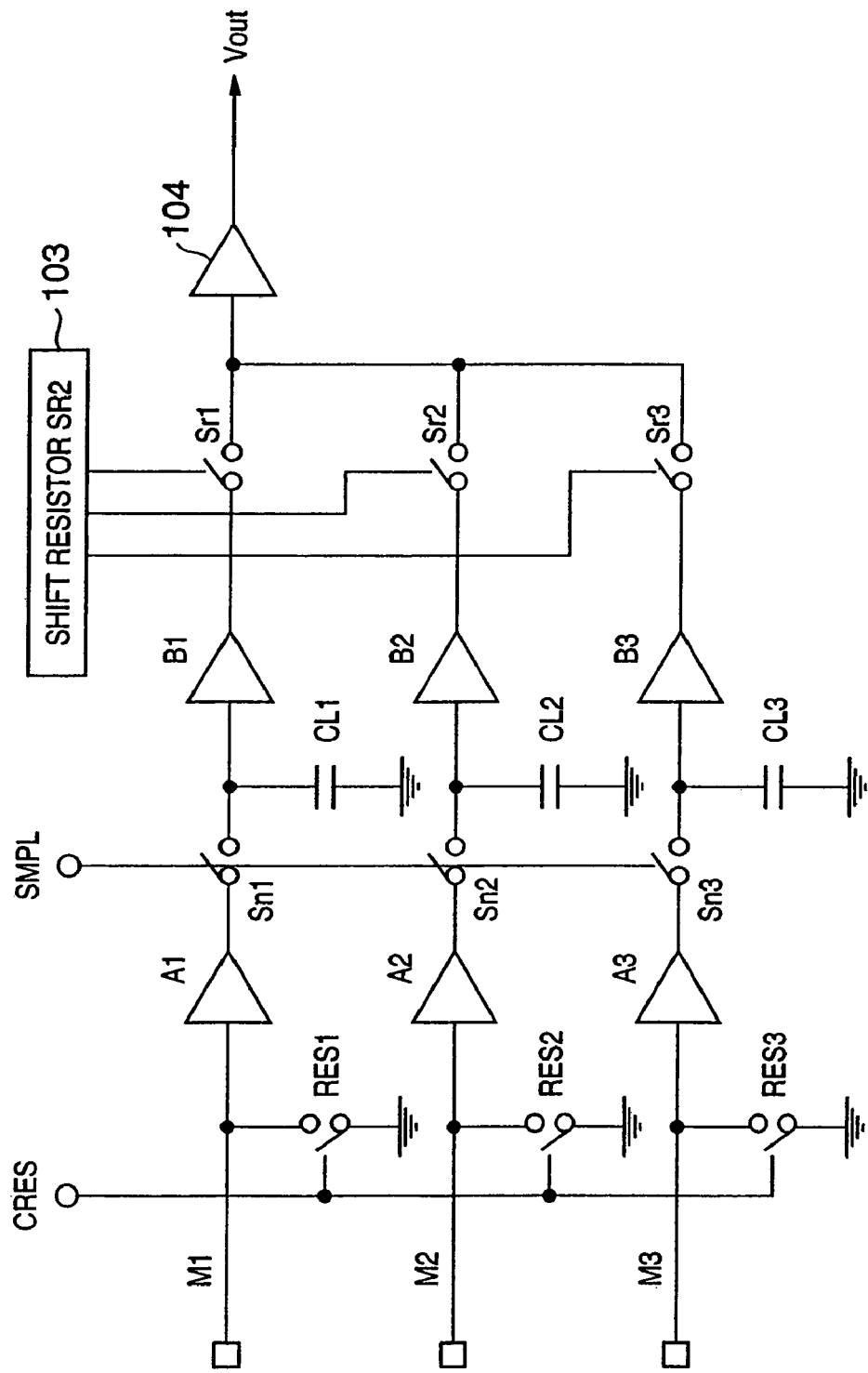
FIG. 2 is a circuit diagram showing the internal structure of the read-out circuit of FIG. 1.

FIG. 2 is a circuit diagram showing the internal structure of the read-out circuit of FIG. 1. In FIG. 2, RES1–RES3 are reset switches that reset the signal lines M1–M3, A1–A3 are amps that amplify the signals in M1–M3, CL1–CL3 are sample-hold capacitors that temporarily store the signals amplified by amps A1–A3, Sn1–Sn3 are sample-hold switches, B1–B3 are buffer amps, Sr1–Sr3 are switches for the serial conversion of parallel signals, reference numeral 103 denotes a shift resister for applying pulses to the switches Sr1–Sr3 for serial conversion, and reference numeral 104 denotes a buffer amp for outputting the serially converted signals.

Figure 3:
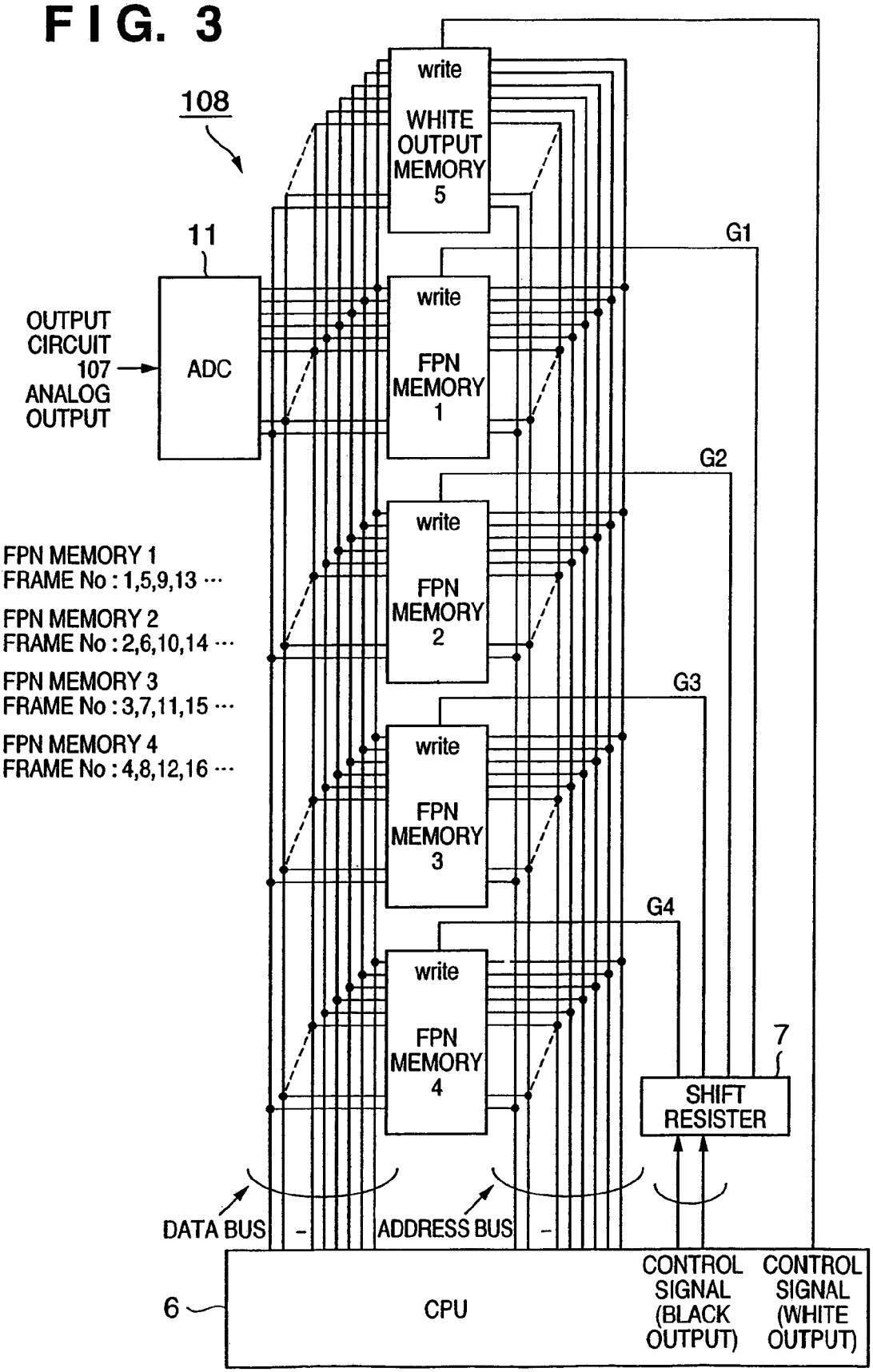
FIG. 3 is a schematic diagram showing the internal structure of the signal processing circuit of the X-ray imaging apparatus of FIG. 1.

FIG. 3 is a schematic diagram showing the internal structure of the signal processing circuit of the X-ray imaging apparatus of FIG. 1. The signal processing circuit 108 is composed of an AD converter that converts the analog output from the read-out circuit 107 to digital output, FPN memories 1–4 for storing N=4 times' worth of dark output (FPN output), a light output memory 5 for storing light output by read-out after X-ray exposure, a CPU 6 that controls the signal processing circuit 108 and signal-processes the data stored in the FPN memories 1–4 and the light output memory 5 in the ways described in detail below, and a shift resister 7 controlled by the CPU 6.

Figure 4:
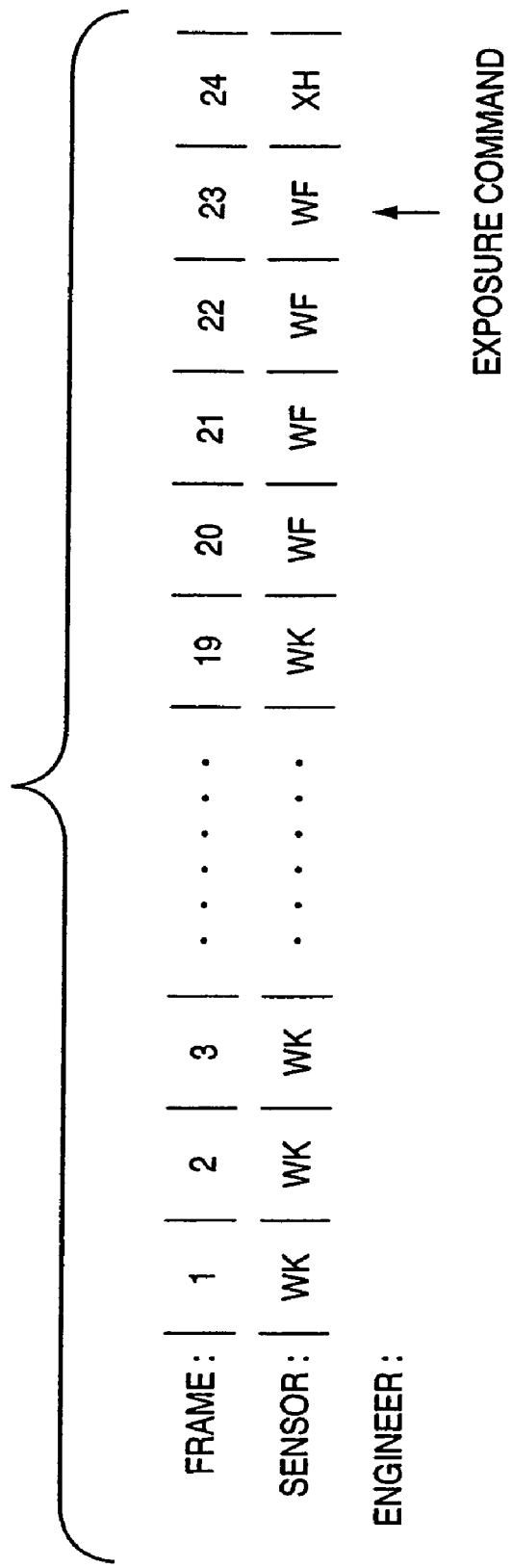
FIG. 4 is a timing chart of the operation of an imaging apparatus according to one embodiment of the present invention.
Figure 7:
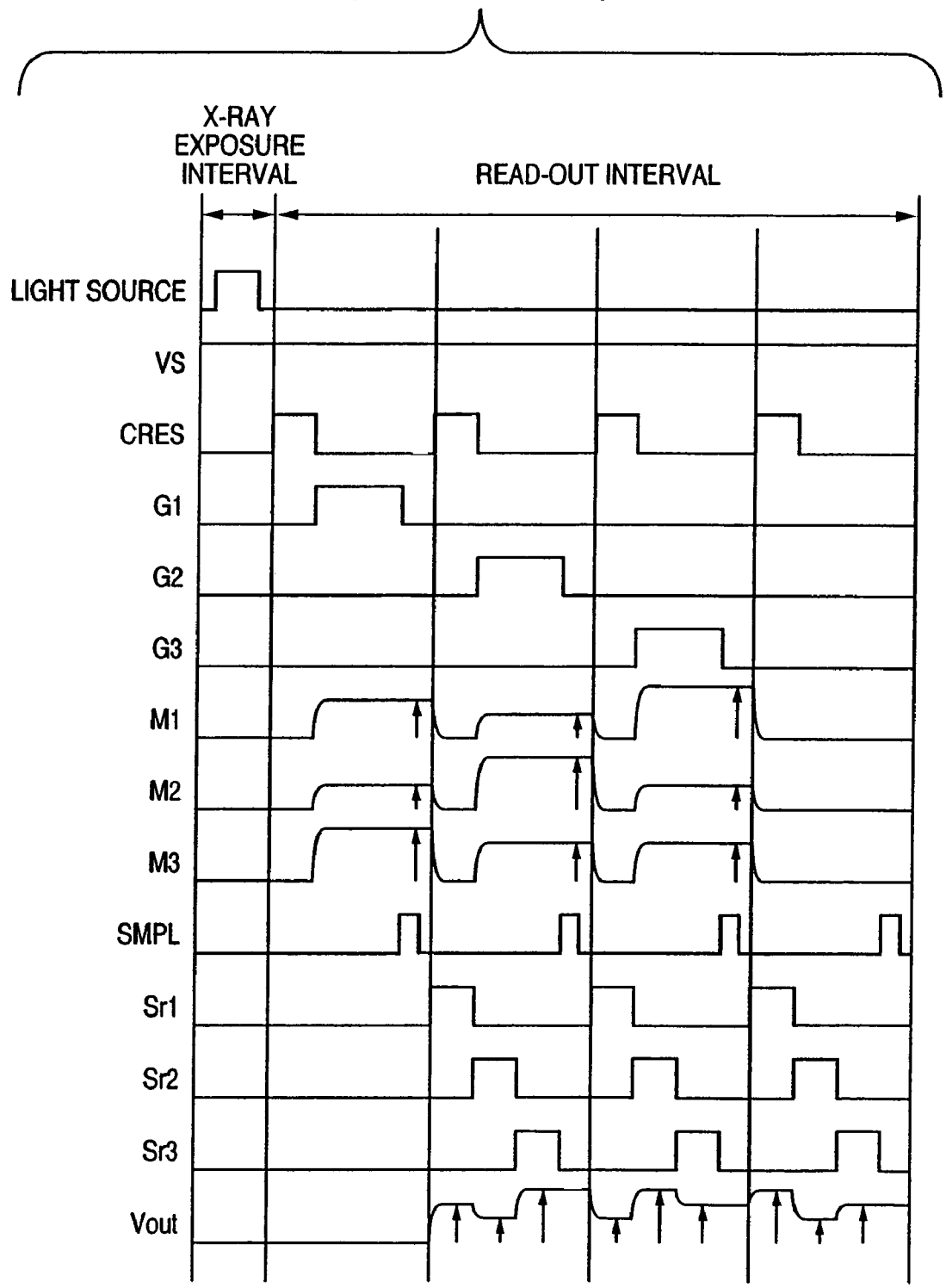
FIG. 7 is a timing chart showing the operation of a conventional X-ray imaging device.

FIG. 4 is a timing chart of the operation of an imaging apparatus according to one embodiment of the present invention. In this example, there are 24 frames and the dark output is read four times as the process proceeds from left to right. The X-ray exposure interval shown in the timing chart of FIG. 7 is denoted by the reference symbol X in FIG. 4, and the read-out interval of FIG. 7 is shown as "H" in FIG. 4. "H" is the light output read-out interval. In FIG. 4, "X" and "H" are written at the 24th frame. "W" denotes the same time interval as the X-ray exposure period, but without the X-ray exposure; it is a "wait" interval in which the photoelectric converters "store darkness", so to speak. "K" and "F" denote a read-out after the wait interval, with the photoelectric converters operating exactly as they do during interval "H". "K" and "H" denote exactly the same read-out operation, the only difference being whether or not they are used as information for acquiring an X-ray image. "K" is called an "empty read" interval or empty read operation and "F" is called a FPN read interval or FPN read operation. As information of acquiring an X-ray operation, "F" is used.

A description is now given of the operation of the X-ray imaging apparatus described above with reference to FIG. 4, in-which the dark output read operation is performed four times.

First, the X-ray imaging apparatus is caused to perform "W" and "K" operations alternately. At this time, at the actual imaging site, the radiologist (or X-ray technician, as the case may be) positions that part of the patient's body (that is, the subject) to be imaged atop the light-sensing surface of the X-ray imaging apparatus. Since it is not known when an X-ray will next be taken, the dark output information of the empty read "K" of this interval is stored in the signal processing circuit 108. Once the radiologist or X-ray technician has properly positioned the patient and completed preparation for imaging, the order is given for the X-ray imaging apparatus to expose, at which point the X-ray imaging apparatus performs the wait operation "W" and the empty read operation "K" (actually "F" but for convenience called "K"), then shifts to the X-ray exposure interval "X", and finally performs the light output read-out operation "H".

When imaging is finished, the four empty read operations "K" performed just prior to the present read-out operation are used as FPN correction information, denoted by "F" in FIG. 4. In this case, the empty read operations of frame nos. 21, 22 and 23 are "F". However, at the time operation commences, it cannot be determined in advance which empty read operation "K" will be used for the FPN read operation "F", so in essence the "F" immediately preceding the "H" is used when the read operation "H" is finished by the exposure order issued by the radiologist or X-ray technician.

Therefore, the information from "K" from the start of imaging must be stored in memory. However, since it is not known whether the exposure command will be issued immediately after operation begins, it makes no sense to store all the FPN in memory because doing so takes up a large amount of memory capacity.

In order for the signal processing circuit 108 shown in FIG. 3 to store the analog output from the X-ray imaging apparatus, the analog output from the read-out circuit 107 must first must be converted into digital output at the AD converter 11 and stored in the FPN memories 1–4 and the light output memory 5. The AD converter output is connected in parallel to the data lines of each of the five memories described above. The CPU 6 data bus is also connected to the data liens of each of the five memories described above. At the same time, the CPU 6 address bus is connected to the address lines of each of the five memories described above. The chronologically output N=4 times' worth of dark output (FPN output) is then stored in the respective memories by the output signals (G1–G4) output by the shift resister 7 which is controlled by the CPU 6. Each time the number of frames increases, the CPU 6 causes the shift resister 7 shifts the output signals in the order G1→G2→G3→G4, and returning once again to G1 output signal after the G4 output signal has been output. Therefore, a continuous 4-time empty read operation "K" output is always being stored in the respective memories. In other words, even when all four memories have been written to, so long as there is no exposure command issued new dark output data is successively stored in the memories. After an exposure command has been issued and the process proceeds to the X-ray exposure interval, the operation of writing data to the FPN memories is completed. The data that is stored in the FPN memories 1–4 then becomes the N=4 times' worth of dark output data immediately preceding the light output read-out operation "H".

After the X-ray exposure interval is completed, the light output data output by the read-out operation "H" is then stored in the light output memory 5 by a light output control signal from the CPU 6.

Figure 5:
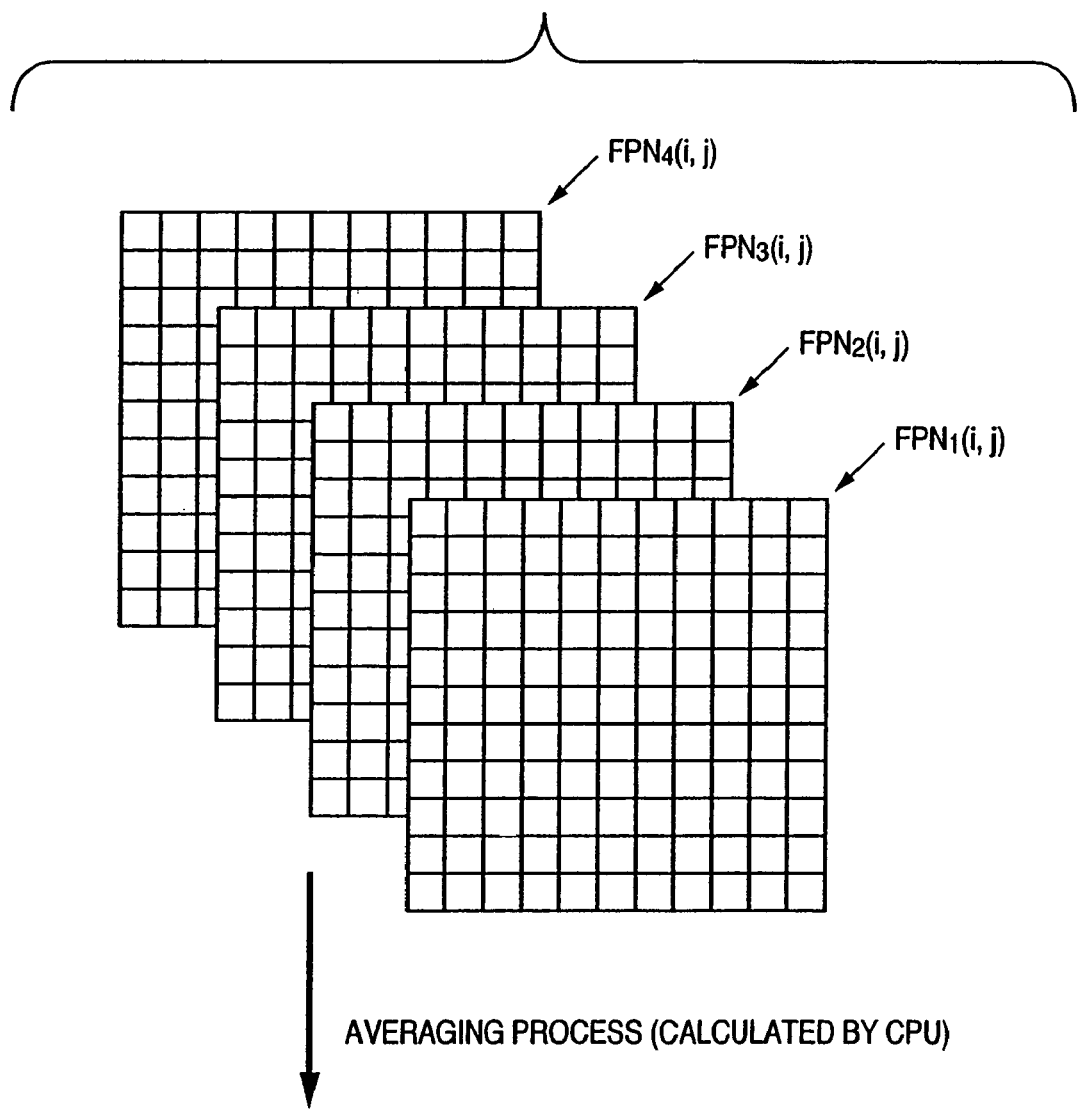
FIG. 5 is a schematic diagram showing steps in a process of averaging two continuous pieces of FPN data according to one embodiment of the present invention.

FIG. 5 is a schematic diagram showing steps in a process of averaging two continuous pieces of FPN data according to one embodiment of the present invention. FPN data corresponding to the pixels arranged in a 2-dimensional array is stored in the respective FPN memories 1–4. The CPU 6 then acquires FPN data for each of the respective pixels via the data bus described above. The CPU 6 can easily average the four dark output operation values acquired as described above. The averaging process or operation referred to here means simply adding four times' worth of FPN to each of the respectively pixels and dividing the sum by 4. The (average) value thus computed by the CPU may either be stored easily in memory or written over any data already present in any of the FPN memories 1–4.

The averaged correction FPN data calculated by the CPU 6 as described above is then subtracted from each of the pixels. The light output data and the correction FPN data are both acquired by the CPU 6 via the data bus, with the latter then be subtracted fro the former to obtain a corrected result.

By the above-described process, an FPN-corrected, random noise-suppressed X-ray image data can be produced.

As described above, according to the imaging apparatus of the present embodiment, when performing see-through imaging of a subject, the apparatus corrects the fixed pattern noise generated during the process of forming that see-through image of the subject and in so doing also suppresses increases in random noise generated by the photoelectric converter circuit 101 and the read-out circuit 107, thereby providing a radiological imaging method and apparatus with improved reliability.

(Variation)

A description is now given of a variation of the embodiment described above, with reference to FIG. 6.

Figure 6:
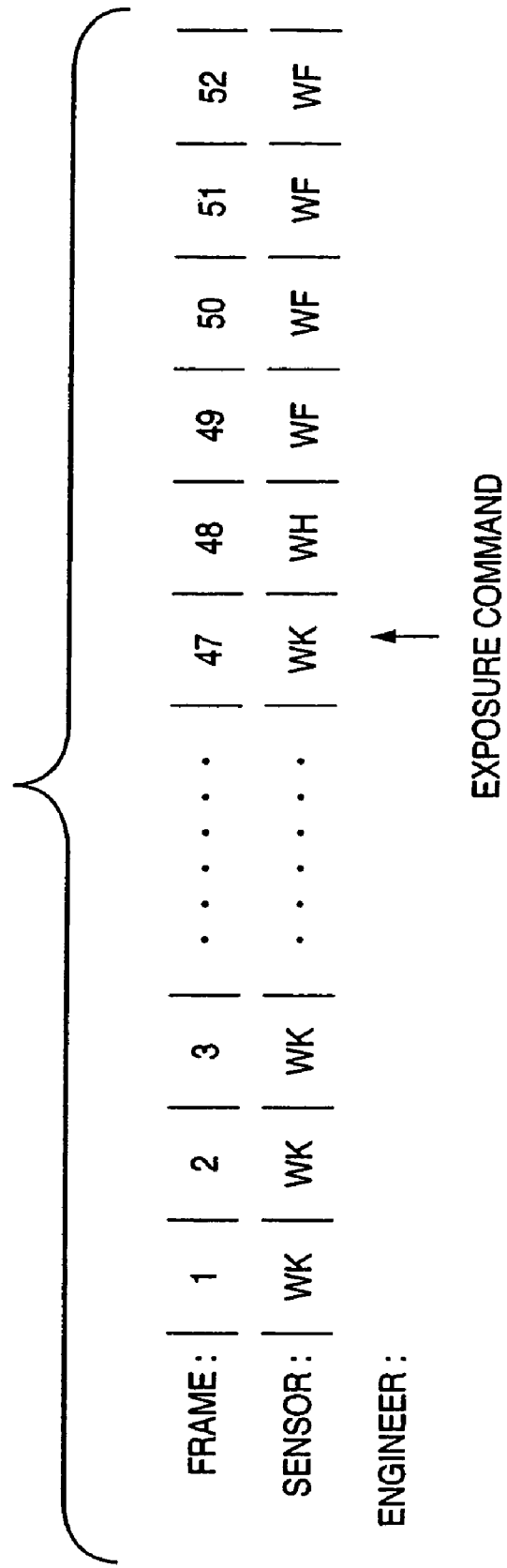
FIG. 6 is a schematic diagram showing steps in a process of averaging two continuous pieces of FPN data according to a variation of an embodiment of the present invention.

FIG. 6 is a schematic diagram showing steps in a process of averaging two continuous pieces of FPN data according to a variation of an embodiment of the present invention. FIG. 6 shows an example in which the dark output read-out operation is carried out twice. First, the X-ray imaging apparatus causes the "W" and "K" operations to be performed, at which time, at the actual imaging site, the radiologist (or X-ray technician, as the case may be) positions that part of the patient's body (that is, the subject) to be imaged atop the light-sensing surface of the X-ray imaging apparatus. Unlike the imaging apparatus and method according to the first embodiment, in this variation thereof the dark output information of the empty read operation "K" of this interval is not stored in memory. Once the radiologist or X-ray technician has properly positioned the patient and completed preparation for imaging, the order is given for the X-ray imaging apparatus to expose, at which point the X-ray imaging apparatus performs the wait operation "W" and the empty read operation "K" (actually "F" but for convenience called "K"), then proceeds to the. X-ray exposure interval "X" and then proceeds to the light output read-out operation "H". Immediately after the light output read-out operation is finished, the wait operation "W" and the read-out operation "H" are each performed twice, thus completing the imaging process. The two empty read operations performed immediately after the light output read-out operation "H" are stored in memory and, since they are used as dark output correction data (that is, FPN correction data), are denoted in FIG. 6 by the reference symbol "F".

In the radiological imaging apparatus of the present embodiment, if the standard deviation of the random noise included in the dark output image obtained by the "dark output read-out operation" is $\sigma 1$, then the standard deviation included in the dark output image after carrying out such "dark output read-out operation" N times and averaging the results is $\sigma 1/mt;epmrl;\sqrt{rlxmx}N$.

If the standard deviation of the random noise included in the light image output obtained by the "light output read-out operation" is $\sigma 2$, then the standard deviation $\sigma t$ of the random noise included in the ultimate radiological image after calculating from the light image output the dark output image using the above-described averaging is $$\sigma t = \{\sigma 2^2 + (\sigma 1/\sqrt{N})^2\}^{1/2}.$$

Here, the shot noise of the radiation included in the actual light image output is not needed here and is ignored. The σ2 of the random noise included in the light image output is the same as the σ1 included in the dark image output, so, if this is set simply at σ, then:

$$\sigma t = \sigma (1 + 1/N)^{1/2}.$$

In the conventional case where N=1, random noise of σt=1.41 is improved with each averaging N such that, at N=2, σ=1.22, at N=3, σt=1.15, at N=4, σt=1.11.

Also, in the present invention, the dark image output read-out operation is carried out just before or just after the light image output, and so is not affected by the factors that cause fluctuations in fixed pattern noise such as the passage of time or changes in the ambient temperature,.making it possible to provide a radiological imaging apparatus with very high correction accuracy.

The N=2 times' worth of FPN data "F" are afterwards averaged for each of their respective corresponding pixels to produce one frame of dark output data (FPN correction data). The averaged FPN correction data, is subtracted from the light output data of the light output read-out operation "H" for each respective corresponding pixel to obtain an FPN-corrected, improved X-ray image data.

Figure 8:
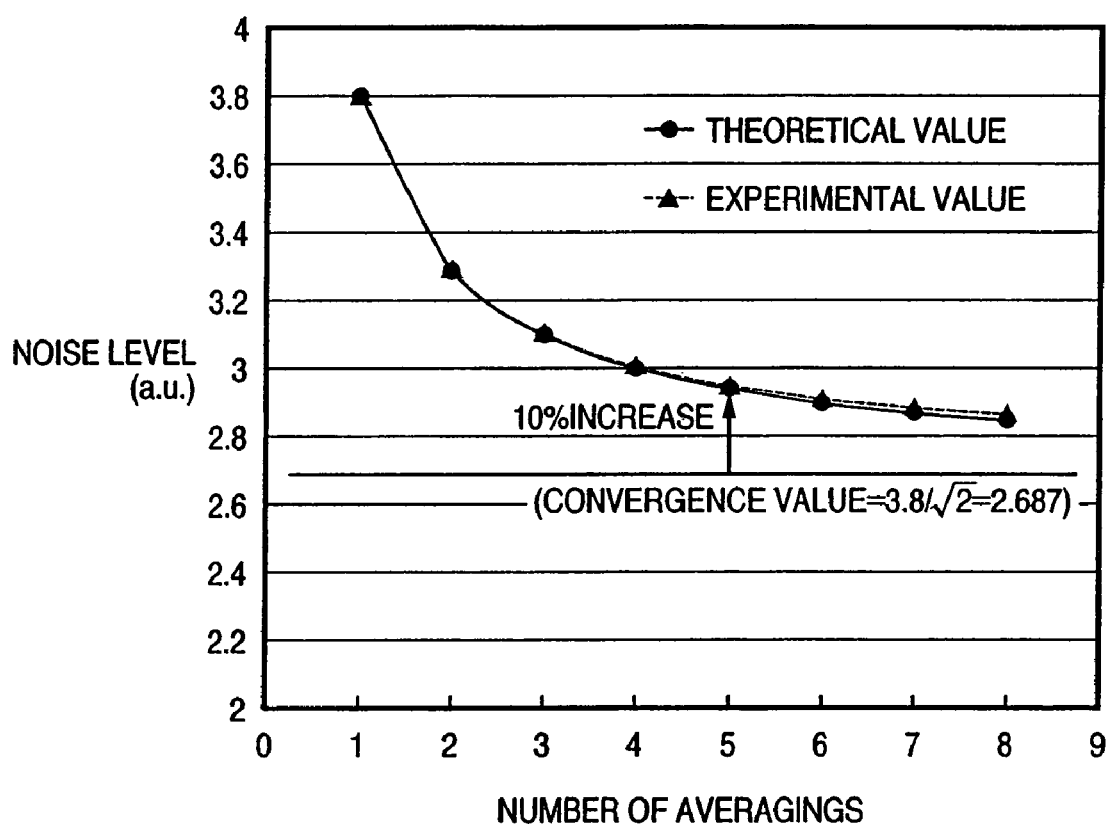
FIG. 8 shows actual measurements of noise level versus number of averaging processes using the X-ray imaging apparatus.

FIG. 8 shows experimental and theoretical measurements of noise level versus number of averaging processes using the X-ray imaging apparatus. The radiological imaging apparatus is provided with a radiation detection means in which 7.2 million pixels are arranged in a 2-dimensional array, drive means, signal read-out means and signal processing means. In a first read-out operation, although in actual usage the apparatus reads the X-rays that pass through the subject, in order to show the noise reduction effect here, read-out is performed in a completely dark environment. Similarly, a second read-out operation is also conducted under the same blacked-out conditions, for a total of eight measurements in all. In FIG. 8, the horizontal X axis represents the number of averagings performed in the second read-out operation and the vertical axis represents the standard deviation of 7.2 million pixels after subtracting the second read-out operation data (averaged data) from the first read-out data. Incidentally, a conventional example is shown where the number of averagings is 1 on the horizontal axis. In this case, no averaging is performed because there is only one data. From FIG. 8, it is experimentally confirmed that making the number of averagings ≧2 reduces noise, ultimately converging at $1/\sqrt{2}$ of noise level (3.8) when n=1. The extent of the improvement due to averaging is greatest when the number of averagings is 2, producing a 22.4 percent decrease in noise compared to a conventional example in which n=1 ($\sqrt{2}$=41.4 percent increase). Where n=3, the increase is 15.5 percent. As the number of averagings increases there is a convergence toward the theoretical value (3.8÷$\sqrt{2}$=2.687), but increasing the number of averagings also increases the processing time, so there is a trade-off between noise and speed. As can be understood from FIG. 8, as the number of averagings increases the noise level also decreases, but the effect lessens as the number of averagings increases. In an image including random noise, if there is a 10 percent increase with respect to the convergence value (that is, theoretical value) for that random noise, there is no major deterioration in picture quality, and moreover, is within the factory production S/N tolerance range. In other words, with a maximum of five averagings (n=5), the object of the present invention can be achieved, and conversely, performing greater than five averagings actually contributes to decreased utility. Accordingly, 2–5 averagings is an optimal range, in which noise is greatly reduced in little processing time.

As described above, according to the present variation, when performing see-through imaging of a subject, the apparatus corrects the fixed pattern noise generated during the process of forming that see-through image of the subject and in so doing also suppresses any increase in random noise generated by the photoelectric converter circuit 101 and the read-out circuit 107, thereby providing a radiological imaging method and apparatus with improved reliability.

According to the above-described radiological imaging apparatus and method, the dark output including FPN is subtracted from the light output which includes the X-ray imaged so as to provide a radiological imaging method and apparatus with improved reliability.

Moreover, according to the radiological imaging apparatus and method of the present invention, the dark output containing FPN is acquired either just before or just after imaging of the light output containing the X-ray image, so FPN correction accuracy is high.

Further, since FPN data, which has been averaged over multiple dark outputs, is used to carry out FPN correction, increases in random noise attendant upon FPN correction can also be suppressed, thus improving the quality of the radiological image.

As many apparently widely different embodiments of the present invention can be made without departing from the spirit and scope thereof, it is to be understood that the invention is not limited to the specific preferred embodiments described above thereof except as defined in the claims.

What is claimed is:

1. A computer program for controlling a radiological imaging system including a computer executing said program, a radiation source, and a radiation detection unit having a plurality of photoelectric converters arrayed in a matrix-like formation for detecting and converting radiation originated from the radiation source into electrical signals, the program comprising code for performing the following steps:

a first reading step of reading the electrical signals output by the radiation detection unit, in which the radiation detection unit is operated with applying the radiation originated from the radiation source;

a second reading step of reading the electrical signals output by the radiation detection unit, in which the radiation detection unit is operated without applying the radiation, wherein said second reading step is performed at least twice;

an averaging step of avenging the results of said second reading step so as to obtain an average signal value thereof; and a subtraction step of subtracting the average signal value from a signal value obtained at said first reading step.

2. The program of claim 1, wherein said second reading step is performed at least twice before said first reading step.

3. A computer readable medium containing the computer program of claim 2.

4. The program of claim 1, wherein said second reading step is performed at least twice after said first reading step.

5. A computer readable medium containing the computer program of claim 4.

6. A computer readable medium containing the computer program of claim 1.

* * * * *